US006479679B1

(12) United States Patent
Zygmunt et al.

(10) Patent No.: US 6,479,679 B1
(45) Date of Patent: Nov. 12, 2002

(54) TWO-STEP CONVERSION OF PROTECTED TAXANE ESTER TO PACLITAXEL

(75) Inventors: Jan Zygmunt, Longmont; James D. McChesney, Boulder, both of CO (US)

(73) Assignee: NaPro BioTherapeutics, Inc., Boulder, CO (US)

( * ) Notice: Subject to any disclaimer, the term of this patent is extended or adjusted under 35 U.S.C. 154(b) by 0 days.

(21) Appl. No.: 09/843,284

(22) Filed: Apr. 25, 2001

(51) Int. Cl.[7] ...................... C07D 305/14; C07D 493/12
(52) U.S. Cl. ........................................ 549/510
(58) Field of Search ........................................ 549/510

(56) References Cited

U.S. PATENT DOCUMENTS

| 4,814,470 A | 3/1989 | Colin et al. |
| 4,857,653 A | 8/1989 | Colin et al. |
| 4,924,011 A | 5/1990 | Denis et al. |
| 4,924,012 A | 5/1990 | Colin et al. |
| 4,960,790 A | 10/1990 | Stella et al. |
| 5,015,744 A | 5/1991 | Holton |
| 5,136,060 A | 8/1992 | Holton |
| RE34,277 E | 6/1993 | Denis et al. |
| 5,684,175 A | 11/1997 | Sisti et al. |
| 5,750,737 A | 5/1998 | Sisti et al. |
| 5,770,745 A | 6/1998 | Swindell et al. |
| 5,973,170 A | 10/1999 | Sisti et al. |

FOREIGN PATENT DOCUMENTS

| EP | 0 400 971 | 12/1990 |
| EP | WO 94/18186 | 8/1994 |
| WO | WO 91/13066 | 9/1991 |

OTHER PUBLICATIONS

"Biologically Active Taxol Analogues with Deleted A–Ring Side Chain Substituents and Variable C–2' Configurations", Swindell et al, *Journal of Medicinal Chemistry,* 1991, vol. 34, No. 3, pp. 1176–1184.
"New and Efficient Approaches to the Semisynthesis of Taxol and Its C–13 Side Chain Analogs by Means of B–Lactam Synthon Method", Ojima et al, *Tetrahedron,* vol. 48, No. 34, pp. 6985–7012, 1992.
"Improved Protection and Esterification of a Precursor of the Taxotere and Taxol Side Chains", Commercon et al, *Tetrahedron Letters,* vol. 33, No. 36, pp. 5185–5188, 1992.
"Highly Stereocontrolled and Efficient Preparation of the Protected, Esterification–Ready Docetaxel (Taxotere) Side Chain", Kanazawa et al, J. Org. Chem, vol. 59, No. 6, pp. 1238–1240, 1994.
"Novel Biologically Active Taxol Analogues: Baccatin III 13–(N–(p–Chlorobenzoyl)–(2'R, 3'S)–3'–phenylisoserinate) and Baccatin III 13–N–Benzoyl–2'R, 3'S)–3'–(p–chlorophenyl) isoserinate)", Georg et al., *Bioorganic & Medicinal Chemistry Letters,* vol. 2, No. 4, pp. 295–298, 1992.

"Application of the Vicinal Oxyamination Reaction with Asymmetric Induction to the Hemisynthesis of Taxol and Analogues", L. Mangatal, et al., *Tetrahedron,* vol. 45, No. 13, pp. 4177 to 4190, 1990.
"Synthesis of Biologically Active Taxol Analogues with Modified Phenylisoserine Side Chains", Georg et al.,*J. Med. Chem.,* 1992; 35, 4230–4237.
"Selectively Reductive Cleavage of the Protected Taxol Side Chain with Sodium Borohydride", *Chemical Abstracts,* vol. 125, No. 21, 1996; C.Z., Yu et al, Abstract No. 276128j, p. 1302.
"Selectively Reductive Cleavage of the Protected Taxol Side Chain with Sodium Borohydride", *Chinese Journal of Chemistry,* vol. 14, No. 4, 1996, pp. 381–384.
"Taxol Chemistry. 7–O–Triflates as precursors to Olefins and Cyclopropanes", Johnson et al., *Tetrahedron Letters,* vol. 35, No. 43, pp. 7893–7896, 1994.
"Alkyl Benzyl Carbonate: $ROCO_2Bn$ (Chart 2)," *Protective Groups in Organic Synthesis,* Greene et al., 2d ed., p. 109, 1991 (Abstract).

*Primary Examiner*—T. A. Solola
(74) *Attorney, Agent, or Firm*—Timothy J. Martin; Michael R. Henson; Mark H. Weygandt

(57) ABSTRACT

The present invention relates to a method of producing paclitaxel from a protected coupled ester compound having a formula:

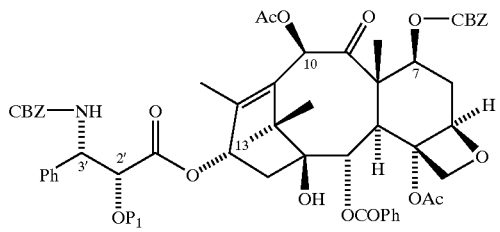

wherein $P_1$ is a hydrogenatable protecting group, comprising the steps of deprotecting the 7-O-position, 3'-N-position and 2'-O-position thereof in the presence of an acid to form a first intermediate compound having a formula:

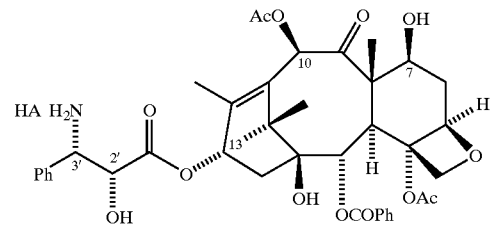

wherein HA is said acid, and benzoylating the first intermediate compound at the 3'-N-position thereby to produce paclitaxel.

41 Claims, 3 Drawing Sheets

TWO-STEP CONVERSION OF PROTECTED TAXANE ESTER TO PACLITAXEL

FIELD OF THE INVENTION

The present invention is directed to the production of the anti-neoplastic compound paclitaxel. More particularly, the present invention is directed to the production of paclitaxel from a protected coupled ester intermediate, which may be formed by esterifying a protected baccatin III backbone with a suitably protected side chain acid. In particular, the present invention relates to the production of paclitaxel by esterifying 7-CBZ baccatin III with a 3-N-CBZ-2-O-protected-(2R,3S)-3-phenylisoserine to produce a protected coupled ester intermediate that may thereafter be deprotected and N-benzoylated to produce paclitaxel.

BACKGROUND OF THE INVENTION

Various taxane compounds are known to exhibit anti-tumor activity. As a result of this activity, taxanes have received increasing attention in the scientific and medical community. Primary among these is a compound known as "paclitaxel" which is also referred to in the literature as "taxol". Paclitaxel has been approved for the chemotherapeutic treatment of several different varieties of tumors, and the clinical trials indicate that paclitaxel promises a broad range of potent anti-leukemic and tumor-inhibiting activity. Paclitaxel has the formula:

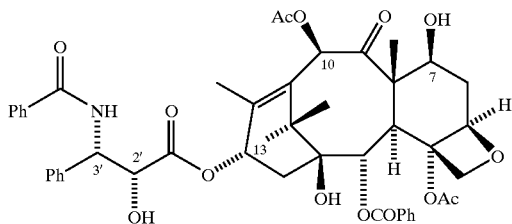

Paclitaxel is a naturally occurring taxane diterpenoid which is found in several species of the yew (genus Taxus, family Taxaceae). Unfortunately, the concentration of this compound in the yew is very low, and the species of evergreen are also slow growing. Even though the bark of the yew trees typically exhibit the highest concentration of paclitaxel, the production of one kilogram of paclitaxel requires approximately 16,000 pounds of bark. Thus, the long-term prospects for the availability of paclitaxel through isolation are discouraging.

While the presence of paclitaxel in the yew tree is in extremely low concentrations, there are a variety of other taxane compounds, such as baccatin III, cephalomanine, 10-deacetylbaccatin III, etc., which are also able to be extracted from the yew bark and leaves. Some of these other taxane compounds are more readily extracted in higher yields. Indeed, a relatively high concentration of 10-deacetylbaccatin III can be extracted from the leaves of the yew as a renewable resource.

Accordingly, attention has turned to the semi-synthesis of paclitaxel from precursor compounds. In order to successfully synthesize paclitaxel, convenient access to a chiral, non-racemic side chain acid and an abundant natural source of a usable baccatin III backbone as well as an effective means of joining the two are necessary. However, the esterification of the side chain acid to the protected baccatin III backbone is difficult because of the steric hindrance of the 13-hydroxyl which is located in the baccatin III backbone within the concave region of the hemispherically shaped baccatin III skeleton.

Some early synthetic routes in the semi-synthesis of paclitaxel are described, for example, in U.S. Pat. No. 5,770,745 to Swindell et al. The use of protecting groups to protect various positions of the taxane backbone and the side chain acid was investigated as a means of improving the chemical process to form paclitaxel, and of improving the esterification step in particular.

One technique for the semi-synthesis of paclitaxel is found in U.S. Pat. No. 5,750,737 to Sisti et al. As discussed therein, paclitaxel can be synthesized by joining 7-CBZ baccatin III of the formula:

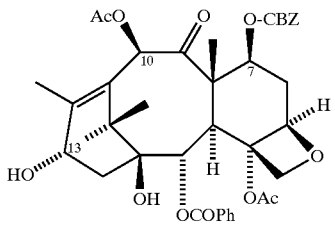

(where CBZ is the "benzyloxycarbonyl" group, —CO$_2$CH$_2$Ph), with 3-N-CBZ-2-O-protected (2R,3S)-3-phenylisoserine of the formula:

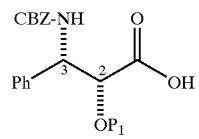

where the 2-hydroxyl is protected by a hydrogenatable benzyl-type group P$_1$ such as benzyloxymethyl (BOM) or benzyl. 7-CBZ baccatin III may be formed through the synthesis and use of 7-metal alkoxide intermediates and analogs of baccatin III, as described, for example, in U.S. Pat. Nos. 5,750,737 and 5,973,170 to Sisti et al. The production of the 3-N-CBZ-2-O-protected (2R,3S)-3-phenylisoserine is taught, for example, in U.S. Pat. No. 5,684,175 to Sisti et al.

Following the esterification of the protected baccatin III with the protected side chain to form a protected coupled ester of the formula:

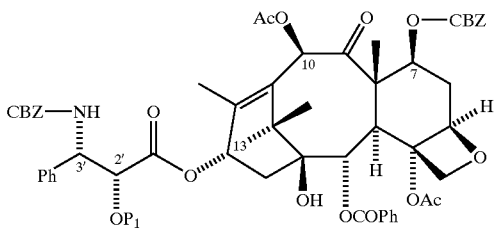

the compound may be suitably deprotected, acylated, and further deprotected to yield paclitaxel. Specifically, the CBZ protecting groups at the 7-O and 3'-N positions are removed, a benzoyl group is added at the 3'-N position and the 2'-O-protecting group is removed. U.S. Pat. No. 5,750,737 describes a deprotection and acylation sequence involving various steps to arrive at the final desired product. In particular, that patent teaches the use of work-ups involving recovery and purification steps (such as filtration, reduction to residue under vacuum, organic phase separation, and the like) in between the various steps. Furthermore, the hydrogenolysis of the coupled ester with Pearlman's catalyst as described therein could take about one day to proceed to completion of the deprotection at the 7-O and the 3'-N positions by removal of the two CBZ groups. Additionally, after benzoylation of the 3'-amino group, the hydrogenolysis of the 2'-O-BOM paclitaxel took several days to complete, and included catalyst replacement as well as isolation and purification of the 2'-O-BOM paclitaxel intermediate. Additionally, factors such as preliminary purification of the 2'-O-BOM-paclitaxel intermediate as well as change of the catalyst and reaction medium contribute to high cost of the hydrogenation process.

While the existing techniques for synthesizing paclitaxel certainly have merit, there is still a need for improved chemical processes that can produce this anti-cancer compound and intermediates useful in the synthesis and semi-synthesis thereof. In particular, it is desirable to provide efficient processes requiring shorter times and fewer steps while still providing acceptable yields in the semi-synthesis of paclitaxel. Accordingly, the present invention is directed to an improved synthesis of paclitaxel or other taxanes from a protected coupled ester intermediate. The present invention teaches a new, useful and more efficient method for the conversion of the protected coupled ester to paclitaxel that may be performed in a single reaction vessel.

SUMMARY OF THE INVENTION

It is an object of the present invention to provide a new and useful method for synthesizing paclitaxel.

It is another object of the present invention to provide new intermediate compounds useful in the production of paclitaxel.

It is a further object of the present invention to produce paclitaxel from a protected coupled ester of the formula:

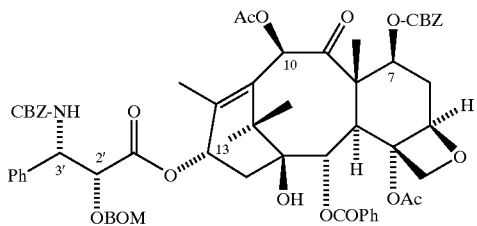

which may be deprotected and N-acylated to yield paclitaxel.

It is yet another object of the present invention to provide methods for producing paclitaxel which are simplified and which may be suitable for large scale production of paclitaxel for anti-neoplastic applications.

It is yet another object of the present invention to improve the efficiency of the hydrogenolytic conversion of a protected coupled ester to paclitaxel.

It is yet another object of the present invention to convert a protected coupled ester to paclitaxel in a single vessel without isolation or purification of a 2'-O-protected paclitaxel intermediate.

According to the present invention, then, a method is provided of producing paclitaxel from a protected coupled ester compound having a formula:

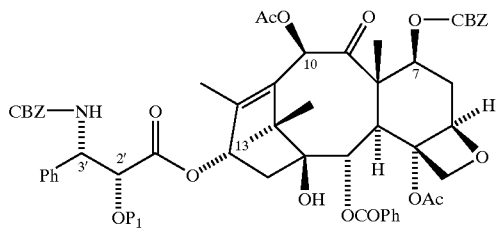

wherein $P_1$ is a hydrogenatable protecting group, such as benzyl, substituted benzyl, benzyloxymethyl, or benzoyl. The method comprises the steps of deprotecting the 7-O-position, 3'-N-position, and 2'-O position of the protected coupled ester compound in the presence of an acid to form a first intermediate compound having a formula:

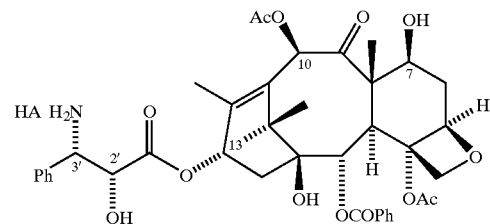

wherein HA is the acid, and benzoylating the 3'-N-position of said first intermediate compound thereby to produce paclitaxel. The acid may be an inorganic or organic acid, and is preferably hydrochloric acid. The protected coupled ester compound is preferably dissolved in a solvent to form a first solution prior to the step of deprotecting the 7-O-position, 3'-N-position, and 2'-O-position of the protected coupled ester compound. The solvent may be one that includes an ether, ester, or alcohol functional group, such as THF, ethyl acetate, methanol or isopropanol. Water is preferably present in said first solution in from 10% to 25% (v/v) of said solvent, and 5 to 20 mol equivalents of the acid is preferably added to the first solution, along with a hydrogenation catalyst such as Pearlman's catalyst or palladium on carbon catalyst, to form a first reaction mixture. The catalyst is preferably 10% Pd/C 50% wet, in an amount of 30% to 80% mass equivalent of said protected coupled ester.

The step of deprotecting the 7-O-position, 3'-N-position and 2'-O position of the protected coupled ester compound is accomplished by hydrogenolytic deprotection by stirring the first reaction mixture under a hydrogen atmosphere for 30 to 60 minutes.

The step of benzoylating the first intermediate compound may be accomplished by mixing benzoyl chloride and triethylamine with the first intermediate compound to form a second reaction mixture. Preferably, 1.20 mol equivalents of benzoyl chloride is mixed with the first intermediate compound, and, after addition of triethylamine, the second reaction mixture is stirred for 30 minutes under an inert atmosphere, such as a nitrogen atmosphere.

The present invention also relates to a method of producing paclitaxel, that comprises the steps of stirring a first reaction mixture including a solvent, an acid, a hydrogenation catalyst and a protected coupled ester compound having a formula:

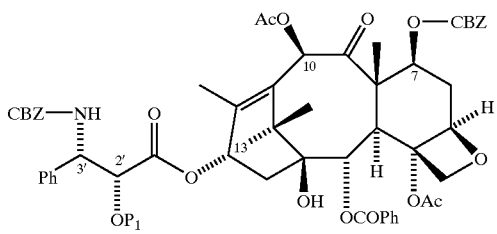

in a reaction vessel under a hydrogen atmosphere, adding a benzoylating agent, such as benzoyl chloride and triethylamine, to the reaction vessel to form a second reaction mixture and stirring the second reaction mixture, such as under an inert atmosphere, thereby to produce paclitaxel. A compound having the formula:

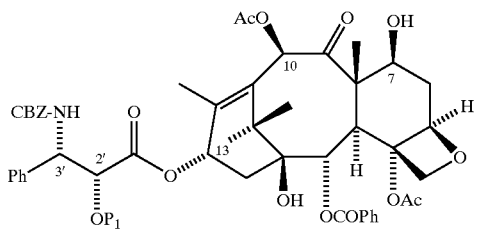

and a compound having the formula:

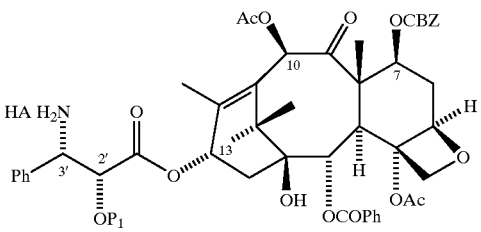

may be formed in the reaction vessel during the step of stirring the first reaction mixture under the hydrogen atmosphere.

Additionally, the present invention is directed to a chemical compound useful in the production of paclitaxel, having the formula:

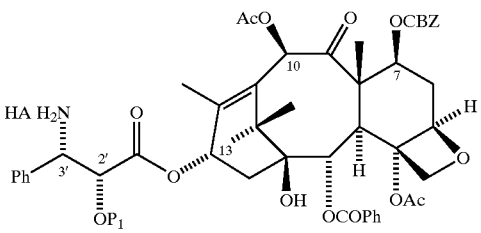

wherein $P_1$ is a hydrogenatable protecting group and wherein HA is an inorganic or organic acid, such as hydrochloric acid, sulfuric acid, trifluoroacetic acid, ptoluenesulfonic acid, camphorsulfonic acid, and the like.

These and other objects of the present invention will become more readily appreciated and understood from consideration of the following detailed description of the exemplary embodiments and the accompanying figures, in which:

DETAILED DESCRIPTION OF THE INVENTION

Figure 1:
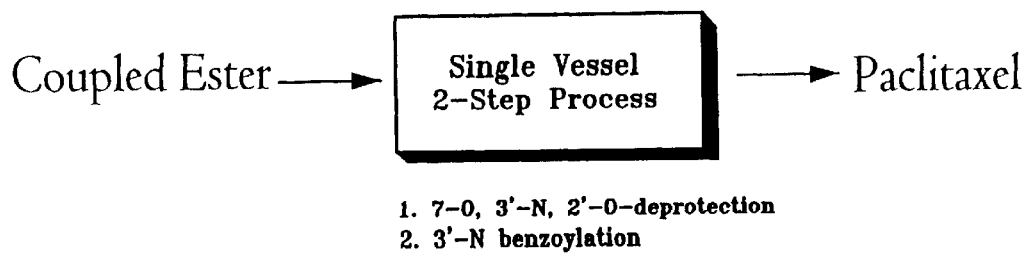
FIG. 1 shows a generalized single vessel 2-step process according to the present invention.

The present invention is broadly directed to a new and useful chemical process for the production of paclitaxel and analogs thereof from a protected coupled ester intermediate. More specifically, the present invention provides an improvement to the chemical conversion of a protected coupled ester to paclitaxel as described in U.S. Pat. No. 5,750,737 to Sisti et al.

In particular, Sisti et al. discusses the formation of a protected coupled ester intermediate, which can have a formula as follows:

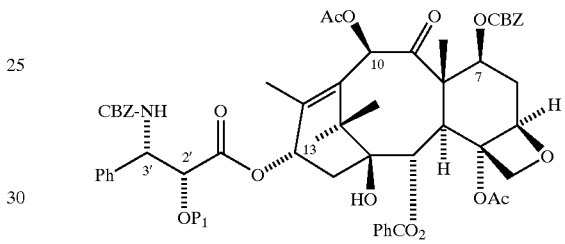

where $P_1$ is a hydrogenatable benzyl-type protecting group. The coupled ester intermediate is then converted into paclitaxel by removing the 7-O-CBZ and 3'-N-CBZ protecting groups, benzoylating the amino group at the 3' position, and removing the 2'-O-benzyl-type protecting group. As discussed in Sisti et al., this is accomplished by first dissolving the coupled ester in isopropanol, adding Pearlman's catalyst, and hydrogenating for twenty-four hours. Thereafter, the mixture is filtered through diatomaceous earth and reduced under vacuum to residue. The residue is either taken up in toluene and anhydrous potassium carbonate is added, or is taken up in ethyl acetate or toluene and a tertiary amine base, such as triethylamine, is added. Benzoyl chloride is then added, and after stirring for two hours, the mixture is washed with water and brine, the resulting organic phase is separated, dried, and concentrated under vacuum. The resulting product is dissolved in isopropanol to which Pearlman's catalyst is added, and the mixture is hydrogenated for 24 hours under 40 psi hydrogen to yield paclitaxel.

In an effort to improve the chemical conversion of coupled ester to paclitaxel, various parameters relating to the hydrogenolysis process were investigated, including the type and amount of catalyst, hydrogen pressure, solvent, presence of acid, temperature and time of reaction. It was found that a Degussa type $Pd(OH)_2/C$ catalyst was one of the most effective catalysts and facilitated significantly the process compared to Pearlman's catalyst and palladium on carbon catalyst. Further investigation of this process showed that introduction of aqueous THF in combination with Pd/C catalyst increases both the yield and the rate of the reaction and at the same time decreases cost of conversion by the use of a cheaper catalyst and by elimination of the use of a costly anhydrous solvent.

Accordingly, as discussed in co-pending application no. XX/XXX,XXX, entitled "Three-Step Conversion of Protected Taxane Ester to Paclitaxel", a single vessel 3-step conversion was developed using benzoic anhydride as the benzoylation reagent. The 3-step conversion comprises first deprotecting at the 7-O and 3'-N positions, next benzoylating at the 3'-N position and thereafter deprotecting at the 2'-O position. That method significantly improved the efficiency of the conversion of coupled ester to paclitaxel by performing all three steps in the same reaction vessel, without change of catalyst and reaction medium, and without isolation and purification of the 2'-O-BOM paclitaxel intermediate.

While the 3-step process provides significant advantages over the former process of conversion, the present invention provides an improved 2-step process which reduces the number of chemical steps in the synthetic process and decreases the total time required therefor. Additionally, the present 2-step process addresses several issues of the 3-step process such as generation of benzoic acid as a by-product and the need for an elevated concentration of acid, such as hydrochloric acid, in the reaction mixture.

I. CONVERSION OF COUPLED ESTER TO PACLITAXEL

Specifically, as shown in FIG. 1, the present invention broadly relates to a single vessel 2-step conversion of a 7-O, 3'-N and 2'-O protected coupled ester to paclitaxel, wherein in a first step the 7-O, 3'-N and 2'-O positions are deprotected, and in a second step the 3'-N position is benzoylated.

Figure 2:
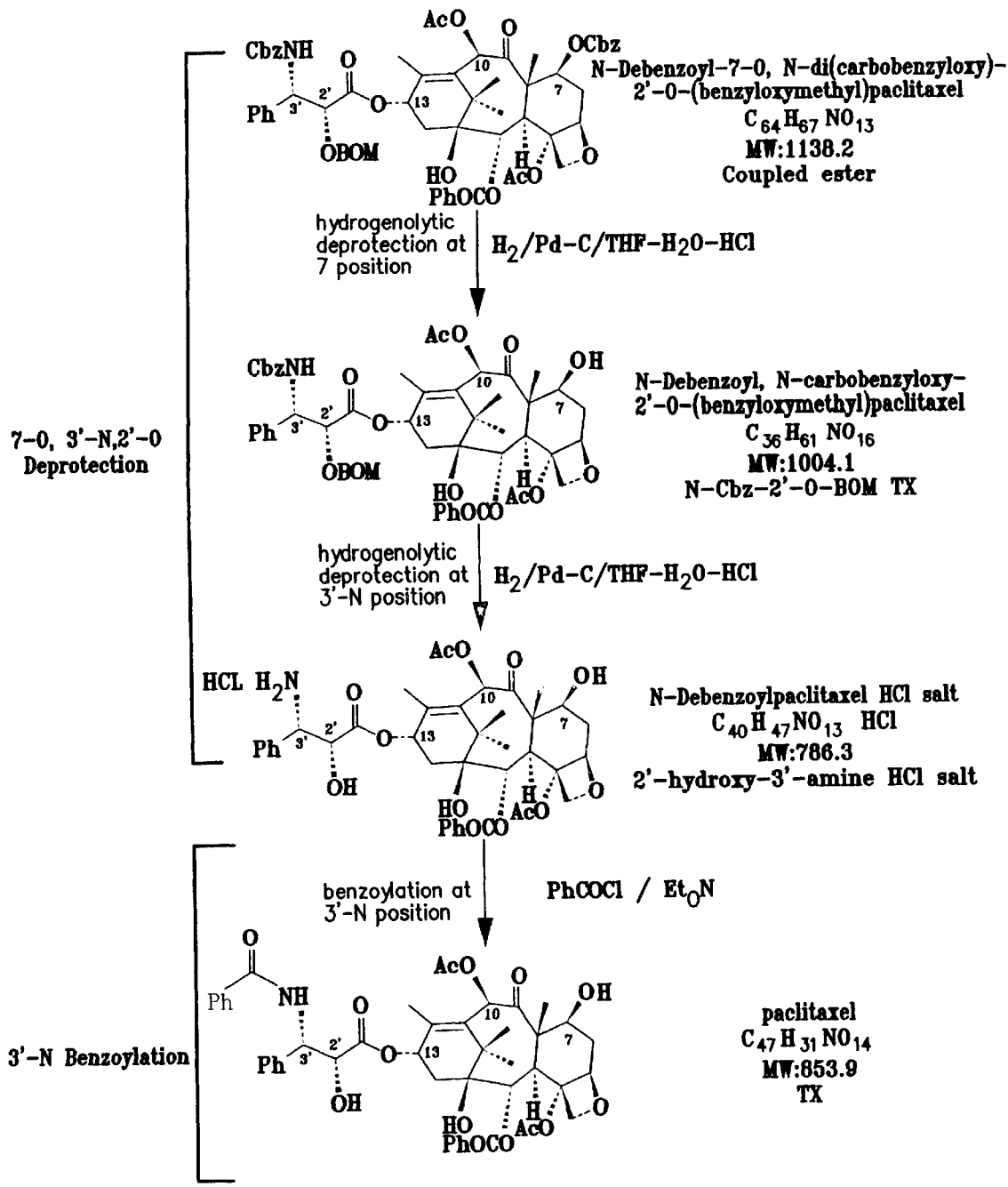
FIG. 2 shows an exemplary preparation of paclitaxel from a protected coupled ester compound according to the present invention.

In the exemplary process, as shown in FIG. 2, the present invention provides a method for converting a 7-O, 3'-N-di-(CBZ), 2'-O-BOM protected coupled ester to paclitaxel via hydrogenolytic deprotection of the molecule at the 7-O, 3'-N, and 2'-O positions (to form a 2'-hydroxy-3'-amine intermediate), followed by benzoylation of the free 3'-amino group to form paclitaxel.

While FIG. 2 shows a 2'-O-BOM protected coupled ester intermediate, such as formed according to the teachings of U.S. Pat. No. 5,750,737, it should be appreciated that other protected coupled ester intermediates may be converted to paclitaxel according to the process shown in FIG. 2. For example, it should be appreciated that while BOM is shown as the protecting group at the 2'-O position in the exemplary process, the method may be applied to a protected coupled ester of the general formula:

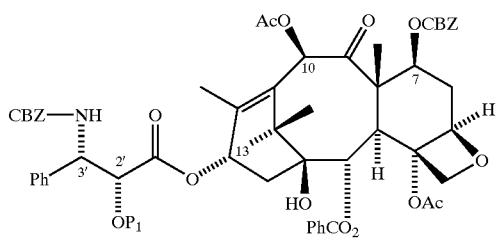

wherein $P_1$ is a hydrogenatable protecting group, such as benzyl, substituted benzyl, benzyloxymethyl, benzoyl, or the like. It should further be appreciated that in addition to the use of other 2'-O-hydrogenatable protecting groups, the present invention contemplates the use of other appropriate protecting groups at the 7-O and 3'-N positions, to the extent understood by the ordinarily skilled person.

1 First Step 7-O, 3'-N, 2'-O Deprotection

The 7-O, 3'-N-di-(CBZ)-2'-O-BOM coupled ester intermediate first undergoes hydrogenolytic deprotection at the 7-O, 3'-N, and 2'-O positions to remove the CBZ groups and BOM group as follows:

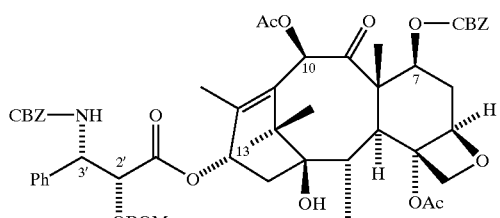

Formula 1

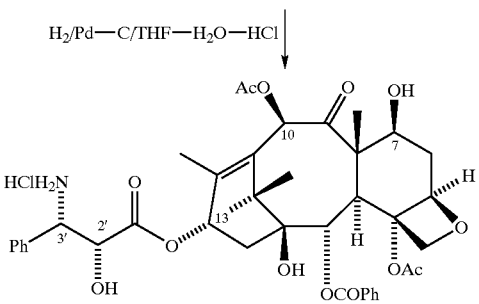

Formula 2

It should be appreciated that a 3'-N-CBZ-2'-O-BOM-7-hydroxy intermediate of the formula:

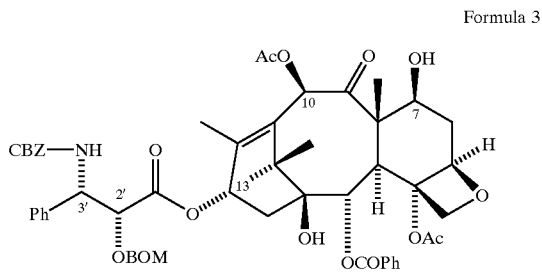

Formula 3 may be formed during this step, as shown in FIG. 2. Additionally, it is believed that a 3'-N-amino-2'-O-BOM-7-O-CBZ paclitaxel intermediate of the formula:

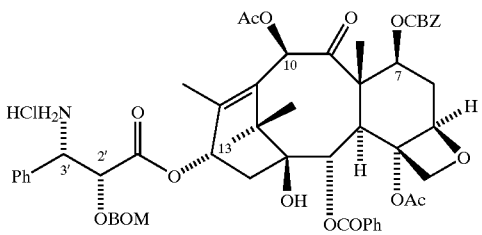

may also be formed during this step.

In the exemplary process, 5.05g (4.44 mmol) of the protected coupled ester of Formula 1 was dissolved in 90.0 mL of THF in a reaction vessel, such as a 0.5 L round bottom flask, equipped with a magnetic stir bar, to which was added 6.10 mL of 3.62 M hydrochloric acid (22.08 mmol) and 8.10 g of 10% Pd/C 50% wet. The reaction vessel was flushed three times with nitrogen and two times with hydrogen, and the reaction mixture was stirred vigorously under an atmosphere provided by a hydrogen filled balloon for about one hour at room temperature. As shown in FIG. 2, this step results in the 7-O, 3'-N, 2'-O hydrogenolytic deprotection of the protected coupled ester of Formula 1 to form a first intermediate compound having Formula 2.

While THF is used in the exemplary process herein, it should be appreciated that other solvents may be used. For example, the present invention contemplates the use of solvents having ether functionalities (such as THF), ester functionalities (such as ethyl acetate), or alcohol functionalities (such as methanol, isopropanol and the like). Additionally, while palladium on carbon catalyst is used in the exemplary hydrogenation reactions, the present invention contemplates other hydrogenation catalysts of palladium, as would be understood by the ordinarily skilled artisan. Further, while hydrochloric acid is used in the exemplary process, the present invention contemplates the use of other acids, including other inorganic and organic acids, such as sulfuric acid, trifluoroacetic acid, p-toluenesulfonic acid, camphorsulfonic acid, and the like.

Hydrogen for the hydrogenation reaction may be supplied by a variety of methods, such as by compressed gas cylinders via a hydrogen line at atmospheric pressure or at higher pressures, or by generation from chemical processes, as would be understood in the art. For example, catalytic hydrogen transfer reduction or transfer hydrogen processes may be used. In particular, the present invention contemplates the use of hydrogen donors, such as ammonium formate, cyclohexene, formic acid, 1,4-cyclohexadiene and cisdecalin, in the presence of Pd/C hydrogenation catalyst.

The present invention contemplates a concentration of water in the solvent of between 10% to 25% (v/v), with 10% of water in THF preferred. Use of between 30% and 80% mass equivalent of the hydrogenation catalyst is contemplated, with 80% mass equivalent of palladium on carbon catalyst preferred. Preferably, 5 to 20 mol equivalents of acid is used, with 5 mol equivalents of hydrochloric acid most preferred. The mixture is preferably stirred vigorously under an atmosphere provided by a hydrogen filled balloon at room temperature or at a temperature of up to the boiling temperature of the solvent for up to 60 minutes.

2. Second Step: 3'-N Benzoylation

The 2'-hydroxy-3'-amine of Formula 2 is next benzoylated at the 3'-N position, as follows:

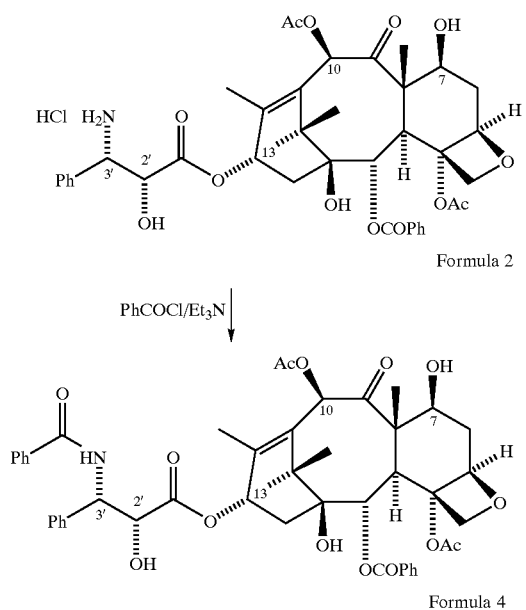

Formula 2

Formula 4

Here, hydrogen was replaced with nitrogen (by flushing the reaction vessel three times with nitrogen) and to the reaction mixture was added 4.65 mL of triethylamine (99%, 33.1 mmol) followed after 2 minutes by addition of 0.625 mL of benzoyl chloride (98%, 5.33 mmol) and the resulting mixture was stirred for 30 minutes.

The mixture was then filtered through Celite (2.5g), the Celite cake was washed with ethyl acetate (200 mL), and the original filtrate and wash were combined into a 1 L separatory funnel and washed with water (3×50 mL), brine (20 mL) and dried over anhydrous magnesium sulfate (2 g). After filtration and rotaevaporation, the product was dried in a vacuum oven for 40 h at 40° C. to give 3.89 g of crude paclitaxel as a white solid.

Samples of reaction products were dissolved in acidified methanol and analyzed by HPLC to give 78.7% paclitaxel by HPLC weight % for a true yield of conversion of 93.1%.

The invention contemplates the use of an excess of benzoyl chloride, and in particular between approximately 1.0 mol equivalents and 2.0 mol equivalents, and specifically 1.2 mol equivalents of benzoyl chloride. Further, while benzoyl chloride is used as the preferred benzoylating agent, it should be appreciated that the present invention contemplates the use of other acylating agents, and benzoylating agents in particular, as would be understood by the ordinarily skilled artisan. It should further be noted that in the exemplary second step, the 2'-hydroxy-3'-amine intermediate is smoothly converted to paclitaxel by reaction with benzoyl choride in the presence of triethylamine, with stirring for about thirty minutes, in the same reaction vessel without removing the catalyst used in the first step, thus providing an efficient method for forming paclitaxel.

II. EXPERIMENTAL RESULTS

Hydrogenation of the coupled ester of Formula 1 in the presence of hydrochloric acid led to the smooth removal of all three protecting groups. N-benzoylation of the resulting 2'-hydroxy-3'-amine intermediate of Formula 2 leads directly to paclitaxel. Therefore, the number of steps in the single vessel conversion of coupled ester to paclitaxel was reduced from 3 to 2 and the formation of 2'-O-BOM paclitaxel as an intermediate was eliminated.

Additional reactions were performed to investigate the effects of varying the amounts of acid and water in the mixture. All hydrogenation reactions were performed under an atmosphere provided by a hydrogen filled balloon at ambient temperature. All small-scale experiments discussed below were performed using 0.20 g of crystallized coupled ester, 86.77 HPLC weight %. In all N-benzoylation reactions, excess of triethylamine and benzoyl chloride were applied, and the formation of 2'-O-benzoyl paclitaxel was minimal.

1. Effects of Different Amounts of Acid on the Conversion of Protected Coupled Ester to 2'-Hydroxy-3'-amine A set of reactions was performed using 0.20 g of the coupled ester of Formula 1 and using hydrochloric acid in different amounts of between 0 and 20 mol equivalents, with results as shown by HPLC data in Table 1, below, and in FIG. 3.

TABLE 1

| HCl | 2'-hydroxy-3'-amine | | | | |
| --- | --- | --- | --- | --- | --- |
| mol eq. | 0 min | 15 min | 30 min | 45 min | 60 min |
| 0 | 0 | — | 3.5 | — | — |
| 2 | 0 | 47.4 | 78.0 | 97.0 | 97.2 |
| 5 | 0 | 93.6 | 98.3 | 98.5 | 97.4 |
| 10 | 0 | 97.6 | 92.6 | 98.4 | 96.9 |
| 15 | 0 | 98.0 | 97.7 | 98.5 | 99.1 |
| 20 | 0 | 93.7 | 96.4 | 98.8 | 94.6 |

Figure 3:
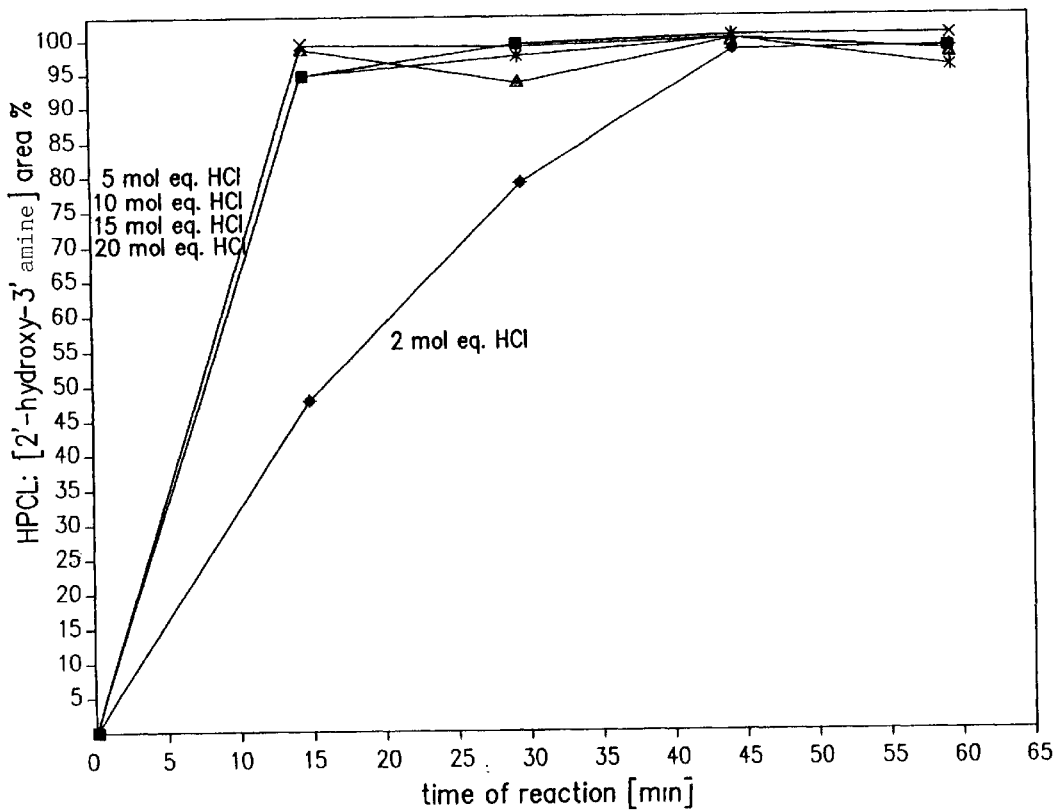
FIG. 3 is a graph showing rates of 2'-hydroxy-3'-amine formation from hydrogenolysis of coupled ester in the presence of different amounts of hydrochloric acid.

The experiments of Table 1 and FIG. 3 were performed using 80% mass equivalent of 1 0% Pd/C in 25% aqueous THF. The reactions were run for one hour and sampled every 15 minutes for HPLC analysis. The presence of hydrochloric acid in the reaction mixture in the range of 5 to 20 mol equivalents caused a remarkable increase in the rate of formation of 2'-hydroxy-3'-amine intermediate from the coupled ester of Formula 1. In particular, when between 5 and 20 mol equivalents of hydrochloric acid was used, all three protecting groups (7-O-CBZ, 3'-N-CBZ and 2'-O-BOM) were removed over 30 to 60 minutes, and the 2'-hydroxy-3'-amine intermediate of Formula 2 was produced. When the 2'-hydroxy-3'-amine intermediate was formed using only 2 mol equivalents of acid, the reaction ran more slowly, as apparent from Table 1 and FIG. 3.

Accordingly, it was found that hydrogenation of the protected coupled ester of Formula 1 in the presence of 5 to 20 mol equivalents of hydrochloric acid and 80% mass equivalent of Pd/C catalyst in 25% (v/v) aqueous THF leads to the rapid removal of all three protecting groups by hydrogenolysis at atmospheric pressure at room temperature (RT). Indeed, in several experiments the reaction was effectively complete after 30 minutes or even 15 minutes, such that it is contemplated that the hydrogenolysis reaction of step 1 could be carried out for durations substantially shorter than one hour, as appropriate.

The chemical stability of 2'-hydroxy-3'-amine intermediate to the hydrogenation conditions was generally satisfactory for at least one hour. However, when 20 mol equivalents of hydrochloric acid was used, a small decrease of the 2'-hydroxy-3'-amine intermediate concentration in the reaction mixture was observed over time.

2. Effects of Different Amounts of Acid on the Conversion of 2'-Hydroxy-3'-amine Intermediate to Paclitaxel After completion of the hydrogenation and replacement of hydrogen with nitrogen, excess triethylamine and 1.2 mol equivalents of benzoyl chloride were added directly to the reaction mixture, and the N-benzoylation reaction was run for 30 minutes, with results as shown by HPLC data in Table 2, below.

TABLE 2

| HCl mol Eq. | 2'-hydroxy-3'-amine | paclitaxel | impurity at ~25 min |
|---|---|---|---|
| 2 | 6.0 | 63.7 | 12.2 |
| 5 | 4.6 | 80.4 | 5.4 |
| 10 | 2.2 | 87.7 | 1.9 |
| 15 | 1.6 | 88.5 | 1.0 |
| 20 | 1.6 | 89.3 | 0.3 |

As shown in Table 2, the second-step conversion of 2'-hydroxy-3'-amine intermediate to paclitaxel is influenced by the number of mol equivalents of the acid used in the first step, which is unexpected because the acid is not involved in the second step and is neutralized by triethylamine before the N-benzoylation is started. Use of fewer mol equivalents of hydrochloric acid in the first step of conversion results in more formation of an impurity at 25 minutes of retention time. Additionally, more 2'-hydroxy-3'-amine intermediate is left unreacted in the N-benzoylation reaction mixture.

The chemical structure of the impurity is predicted from LC-MS data and from consideration of the possible mechanism of formation to be:

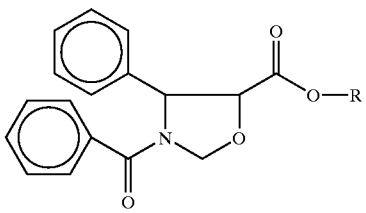

where R represents the baccatin III moiety.

Figure 4:
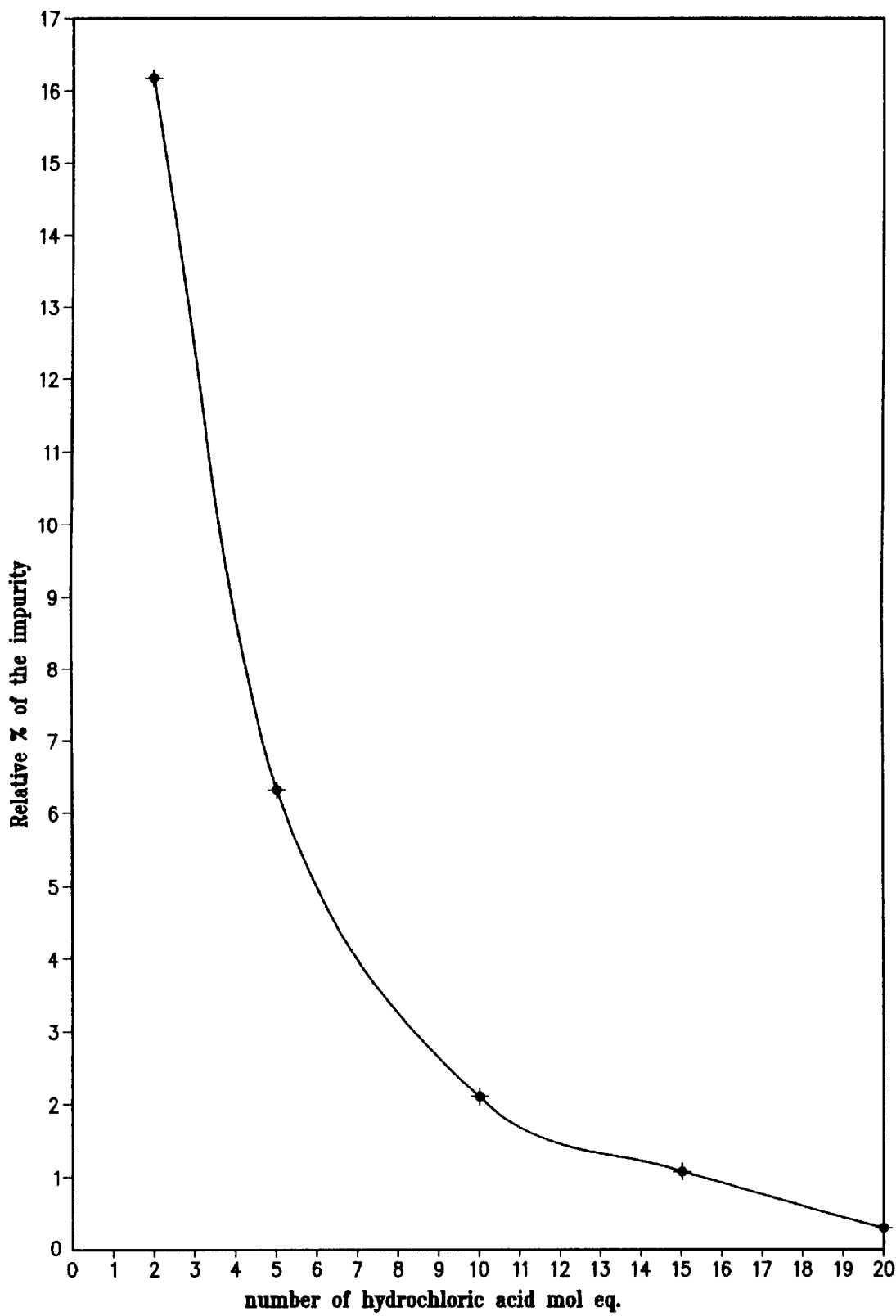
FIG. 4 is a graph showing relative percent of impurity in the post-benzoylation mixture as a function of hydrochloric acid concentration used in the hydrogenation step.

FIG. 4 shows the relative percent of the impurity to paclitaxel as a function of the acid concentration.

As apparent from Table 2 and FIG. 4, the use of fewer mol equivalents of acid in the first step leads to the formation of more impurity in the second step. At 15 to 20 mol equivalents of acid used in the first step, only 1.0% to 0.3% of impurity was formed. However, while the rate of the hydrogenolysis reaction and stability of the 2'-hydroxy-3'-amine intermediate is generally acceptable at the higher levels of acid (Table 1), it is desirable from a cost standpoint to find conditions using lower acid concentrations that still produce low concentrations of impurity.

3. Effects of Different Amounts of Water on the Conversion of Protected Coupled Ester to Paclitaxel Given that more dilute solutions may lower the activity of the benzoylating reagent (triethylamine/benzoyl chloride), experiments were conducted to investigate the effect of different amounts of water on the reactions. Two sets of reactions were performed using 0.20 g of the coupled ester of Formula 1, 80% mass equivalent of catalyst, and 5 mol equivalents of hydrochloric acid at 10% and 28% water, respectively. Results of the hydrogenation reaction are shown by HPLC data in Table 3, and results of the N-benzoylation reaction after 30 minutes are shown by HPLC data in Table 4, below.

TABLE 3

| | Time of hydrogenation | | | | |
|---|---|---|---|---|---|
| % Water | 7 min | 15 min | 30 min | 45 min | 60 min |
| 10% | 74.7 | ~100 | ~100 | 99.2 | 99.4 |
| 28% | 2.4 | 38.4 | 84.3 | ~100 | ~100 |

TABLE 4

| % Water | 2'-hydroxy-3'-amine | paclitaxel | impurity at 25 min |
|---|---|---|---|
| 10% | 1.0 | 91.1 | 0.2 |
| 28% | 6.9 | 74.0 | 7.4 |

As shown in Tables 3 and 4, decreasing the water concentration in the hydrogenation reaction mixture to 10% has a positive effect on both steps. In the hydrogenation reaction, the rate of the reaction is accelerated at 10% water. In the N-benzoylation step, lower water concentration increases the conversion of the 2'-hydroxy-3'-amine intermediate and decreases formation of impurity, thus improving the yield of paclitaxel. By contrast, increasing the water concentration to 28% decreases the rate of the hydrogenation step and decreases the conversion of 2'-hydroxy-3'-amine intermediate and the formation of paclitaxel in the N-benzoylation step. Further, the concentration of the impurity was significantly increased.

To verify the results of this experiment, a scale-up experiment of five grams coupled ester was performed using 5 mol equivalents of hydrochloric acid, 80% mass equivalent of 10% Pd/C catalyst and 10% aqueous THF (v/v) at room temperature for one hour. By HPLC analysis, the hydrogenation step was completed after 30 minutes. No degradation of 2'-hydroxy-3'-amine intermediate in the reaction mixture for the additional 30 minutes was observed. After hydrogen to nitrogen exchange and addition of excess of triethylamine followed by addition of 1.2 mol equivalents of benzoyl chloride, the N-benzoylation step was run for 30 minutes, after which HPLC data indicated 91% of paclitaxel and 2.9% of impurity were formed. The concentration of the 2'-hydroxy-3'-amine intermediate remaining in the reaction mixture was below 1%. The true yield of conversion of the resultant paclitaxel was calculated as 93.1%.

4. Effects of Reverse Addition of Triethylamine and Benzoyl Chloride on Conversion of 2'-Hydroxy-3'-amine Intermediate to Paclitaxel A further approach to improve the efficiency of the reaction is based on reversing the order of addition of the reagents for the N-benzoylation step. Whereas in all previous reactions, triethylamine was added first followed by addition of benzoyl chloride, the reverse addition of benzoyl chloride prior to addition of triethylamine was investigated. Two parallel conversions of coupled ester to paclitaxel were each performed using 10 g of unpurified coupled ester in the presence of 10% water, 5 mol equivalents of hydrochloric acid and 80% mass equivalent of catalyst, with results after 30 minutes as shown by HPLC data in Table 5, below. The non-crystallized unpurified coupled ester was derived directly from the coupling reaction sequence such as that described in Sisti et al, discussed above.

TABLE 5

| Reaction Type | 2'-hydroxy-3'-amine | paclitaxel | impurity at 25 min |
|---|---|---|---|
| Normal: Et$_3$N first, followed by PhCOCl | 2.7 | 60.1 | 8.6 |
| Reverse: PhCOCl first, followed by Et$_3$N | 3.8 | 74.1 | 1.1 |

The change from normal to reverse order of addition of the reagents in the N-benzoylation step significantly reduced formation of the impurity from 8.6% to 1.1% and at the same time increased the yield of paclitaxel from 60.1% to 74.1%. In both cases, similar relative amounts of 2'-hydroxy-3'-amine intermediate were left unreacted in the reaction mixture.

To verify the results of this experiment, parallel scale-up experiments of 10 g unpurified coupled ester were performed using 5 mol equivalents of hydrochloric acid, 80% mass equivalent of 10% Pd/C catalyst and 10% aqueous THF (v/v) at room temperature for one hour. The use of unpurified coupled ester slowed the hydrogenolysis reaction, although still only one hour was needed for complete removal of all three protecting groups. After hydrogen to nitrogen exchange, the first parallel reaction was subjected to the normal order of addition of excess of triethylamine followed by addition of 1.2 mol equivalents of benzoyl chloride, and the second parallel reaction was subjected to the reverse order of addition of 1.2 mol equivalents of benzoyl chloride followed by excess of triethylamine. The N-benzoylation step was run for 30 minutes.

The reaction using the normal order of addition showed a true yield of conversion of 69.9%, whereas the reaction using the reverse order of addition showed a true yield of conversion of 92.8%. Additionally, the reaction using the reverse order of addition yielded 1.1% impurity, which was significantly reduced over the formation of 8.6% impurity in the reaction using the normal order of addition.

The present invention thus provides an improved process for the formation of paclitaxel from a 7-O, 3'-N-di-CBZ, 2'-O-protected coupled ester intermediate. The 2-step procedure provided herein is simple, has a short cycle time, does not require excessive amounts of acid and water and does not produce benzoic acid as a by-product. Reduction of water concentration in the solvent for the first step and using a reverse order of addition of reagents in the second step was found to be effective for decreasing by-product formation.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained therein.

We claim:

1. A method of producing paclitaxel from a protected coupled ester compound having a formula:

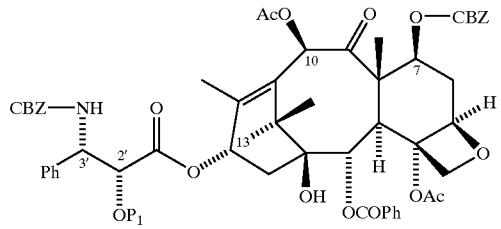

wherein $P_1$ is a hydrogenatable protecting group, comprising the steps of:
(a) deprotecting the 7-O-position, 3'-N-position, and 2'-O-position of the protected coupled ester compound in the presence of an acid to form a first intermediate compound having a formula:

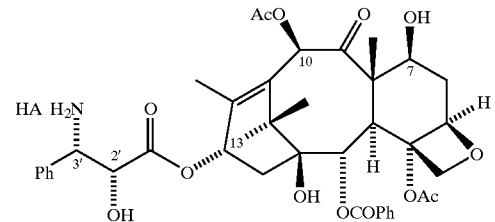

wherein HA is said acid; and
(b) benzoylating said first intermediate compound at the 3'-N-position thereby to produce paclitaxel.

2. A method according to claim 1 wherein $P_1$ is selected from the group consisting of benzyl, substituted benzyl, benzyloxymethyl, and benzoyl.

3. A method according to claim 1 wherein said acid is selected from a group consisting of an inorganic acid and an organic acid.

4. A method according to claim 1 wherein said acid is hydrochloric acid.

5. A method according to claim 1 wherein the protected coupled ester compound is dissolved in a solvent to form a first solution prior to the step of deprotecting the 7-O-position, 3'-N-position, and 2'-O-position of the protected coupled ester compound.

6. A method according to claim 5 wherein said solvent includes a functional group selected from the group consisting of an ether, an ester and an alcohol.

7. A method according to claim 6 wherein said solvent is selected from the group consisting of THF, ethyl acetate, methanol and isopropanol.

8. A method according to claim 5 wherein water is present in said first solution in from 10% to 25% (v/v) of said solvent.

9. A method according to claim 5 wherein from 5 to 20 mol equivalents of said acid is added to said first solution prior to the step of deprotecting the 7-O-position, 3'-N-position and 2'-O-position of the protected coupled ester compound.

10. A method according to claim 5 wherein a hydrogenation catalyst is added to said first solution prior to the step of deprotecting the 7-O-position, 3'-N-position and 2'-O-position of the protected coupled ester compound.

11. A method according to claim 10 wherein said catalyst is selected from the group consisting of Pearlman's catalyst and palladium on carbon catalyst.

12. A process according to claim 10 wherein said catalyst is 10% Pd/C 50% wet.

13. A method according to claim 10 wherein said catalyst is added in an amount of 30% to 80% mass equivalent of said protected coupled ester.

14. A method according to claim 1 wherein the step of deprotecting the 7-O-position, 3'-N-position and 2'-O-position of the protected coupled ester compound is accomplished by hydrogenolytic deprotection.

15. A method according to claim 1 wherein the protected coupled ester compound is dissolved in THF to form a first solution to which said acid and a hydrogenation catalyst are added to form a first reaction mixture prior to the step of deprotecting the 7-O-position, 3'-N-position and 2'-O-position of the protected coupled ester compound, and wherein the step of deprotecting the 7-O-position, 3'-N-position and 2'-O-position of the protected coupled ester compound is accomplished by stirring said first reaction mixture under a hydrogen atmosphere for 30 to 60 minutes.

16. A method according to claim 15 wherein from 5 to 20 mol equivalents of hydrochloric acid is added to said first solution and wherein 10% Pd/C 50% wet is added to said first solution in from 30% to 80% mass equivalent to said protected coupled ester to form said first reaction mixture.

17. A method according to claim 1 wherein the step of benzoylating said first intermediate compound is accomplished by mixing benzoyl chloride and triethylamine with said first intermediate compound to form a second reaction mixture.

18. A method according to claim 17 wherein 1.20 mol equivalents of benzoyl chloride is mixed with said first intermediate compound.

19. A method according to claim 17 wherein said second reaction mixture is stirred for 30 minutes under an inert atmosphere.

20. A method according to claim 19 wherein said inert atmosphere is a nitrogen atmosphere.

21. A method of producing paclitaxel, comprising the steps of:
(a) stirring a first reaction mixture of a solvent, an acid, a hydrogenation catalyst and a protected coupled ester compound having a formula:

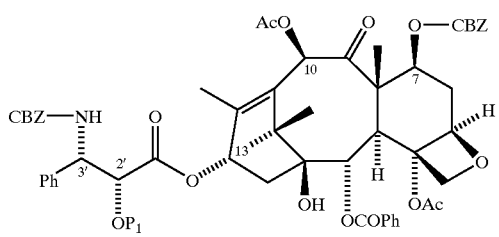

wherein $P_1$ is a hydrogenatable protecting group, in a reaction vessel under a hydrogen atmosphere; and
(b) adding a benzoylating agent to said reaction vessel to form a second reaction mixture and stirring said second reaction mixture thereby to produce paclitaxel.

22. A method according to claim 21 wherein $P_1$ is selected from the group consisting of benzyl, substituted benzyl, benzyloxymethyl, and benzoyl.

23. A method according to claim 21 wherein $P_1$ is benzyloxymethyl.

24. A method according to claim 21 wherein between 5 and 20 mol equivalents of said acid is present in said first reaction mixture.

25. A method according to claim 24 wherein said acid is hydrochloric acid.

26. A method according to claim 21 wherein water is present in said first reaction mixture in 10% to 25% (v/v) of said solvent.

27. A method according to claim 26 wherein said solvent is THF.

28. A method according to claim 21 wherein said catalyst is present in said first reaction mixture in 30% to 80% mass equivalent of said protected coupled ester.

29. A method according to claim 28 wherein said catalyst is selected from the group consisting of palladium-carbon catalyst and Pearlman's catalyst.

30. A method according to claim 21 wherein water is present in said first reaction mixture in 10% by volume of said solvent, wherein 5 mol equivalents of said acid is present in said first reaction mixture, wherein said catalyst is present in said first reaction mixture in 80% mass equivalent of said protected coupled ester, and wherein said first reaction mixture is stirred under an atmosphere of hydrogen at room temperature for 30 to 60 minutes.

31. A method according to claim 30 wherein said solvent is THF, said acid is hydrochloric acid and said catalyst is 10% Pd/C 50% wet.

32. A method according to claim 21 wherein said benzoylating agent is benzoyl chloride and triethylamine.

33. A method according to claim 32 wherein the step of adding said benzoylating agent includes adding benzoyl chloride to said reaction vessel and thereafter adding triethylamine to said reaction vessel.

34. A method according to claim 32 wherein the step of adding said benzoylating agent includes adding triethylamine to said reaction vessel and thereafter adding benzoyl chloride to said reaction vessel.

35. A method according to claim 21 wherein said second reaction mixture is stirred for 30 minutes under an inert atmosphere.

36. A method according to claim 21 wherein a compound having the formula:

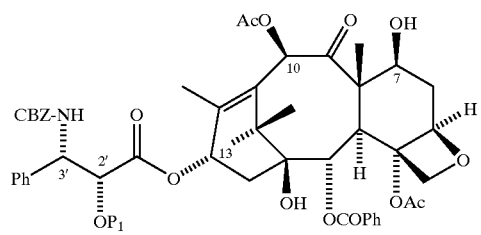

wherein $P_1$ is a hydrogenatable protecting group, is formed in said reaction vessel during the step of stirring said first reaction mixture under said hydrogen atmosphere.

37. A method according to claim 21 wherein a compound having the formula:

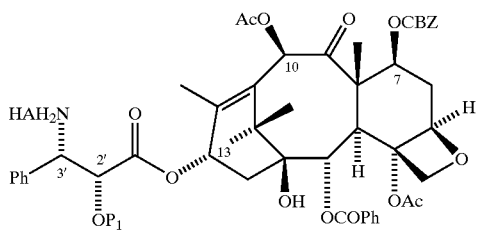

wherein $P_1$ is a hydrogenatable protecting group and HA is said acid, is formed in said reaction vessel during the step of stirring said first reaction mixture under said hydrogen atmosphere.

38. A method of producing paclitaxel from a protected coupled ester compound, comprising the steps of:

(a) stirring a first reaction mixture of 10% (v/v) aqueous THF, a protected coupled ester compound having a formula:

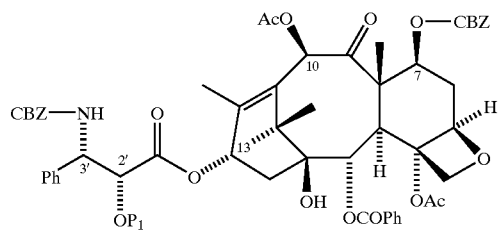

80% mass equivalent of 10% Pd/C catalyst, and 5 mol equivalents hydrochloric acid, in a reaction vessel under a hydrogen atmosphere at room temperature for about one hour, wherein $P_1$ is a hydrogenatable protecting group; and (b) thereafter adding 1.20 mol equivalents of benzoyl chloride and triethylamine to said reaction vessel to form a second reaction mixture and stirring said second reaction mixture under a nitrogen atmosphere for about 30 minutes thereby to produce paclitaxel.

39. A process of producing paclitaxel from a protected coupled ester compound having the formula:

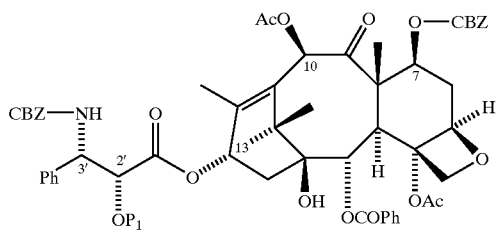

wherein $P_1$ is a hydrogenatable protecting group, consisting of the steps of:

(a) replacing the 7-O-CBZ, 3'-N-CBZ, and 2'-O-$P_1$ groups with hydrogen in the presence of an acid to form a first intermediate compound having a formula:

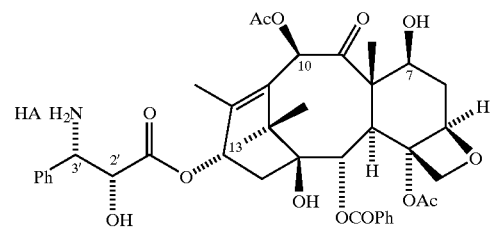

wherein HA is said acid; and (b) benzoylating said first intermediate compound at the 3'-N-position thereby to produce paclitaxel.

40. A chemical compound useful in the production of paclitaxel, having the formula:

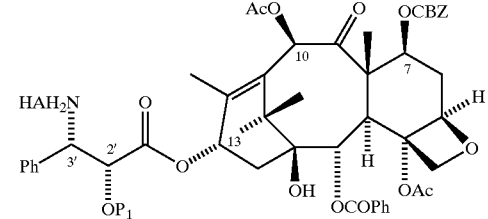

wherein HA is an acid and $P_1$ is a hydrogenatable protecting group.

41. A chemical compound according to claim 40 wherein HA is hydrochloric acid and wherein $P_1$ is benzyloxymethyl.

* * * * *